United States Patent [19]

Cante et al.

[11] Patent Number: 5,258,190
[45] Date of Patent: * Nov. 2, 1993

[54] CALCIUM CITRATE-VEGETABLE OIL COMPOSITIONS

[75] Inventors: Charles J. Cante, Bedford Hills; Emmanuel O. Gbogi, Tarrytown; Fouad Z. Saleeb, Pleasantville, all of N.Y.

[73] Assignee: Kraft General Foods, Inc., Northfield, Ill.

[*] Notice: The portion of the term of this patent subsequent to Mar. 16, 2010 has been disclaimed.

[21] Appl. No.: 29,271

[22] Filed: Mar. 10, 1993

Related U.S. Application Data

[63] Continuation-in-part of Ser. No. 811,193, Dec. 20, 1991, Pat. No. 5,194,270.

[51] Int. Cl.$^5$ .............................................. A23D 9/00
[52] U.S. Cl. ...................................... 426/74; 426/601
[58] Field of Search ............... 426/74, 601, 609, 610, 426/603, 604, 605, 606, 607, 608

[56] References Cited

U.S. PATENT DOCUMENTS 5,028,446  7/1991  Saleeb .................................. 426/74
5,194,270  3/1993  Cante ................................... 426/601

Primary Examiner—Carolyn Paden
Attorney, Agent, or Firm—Linn I. Grim

[57] ABSTRACT

A vegetable oil-based composition containing finely divided special type of calcium citrate salt compositions to produce semi-solid to solid vegetable oil compositions without the use of hydrogenation.

16 Claims, 2 Drawing Sheets

CALCIUM CITRATE-VEGETABLE OIL COMPOSITIONS

This application is a continuation-in-part of application U.S. Ser. No. 07/811,193, filed Dec. 20, 1991, now U.S. Pat. No. 5,194,270.

This invention relates to semi-solid to solid, normally liquid vegetable oil compositions and the use thereof, particularly in the food industry. *Cross Reference* Commonly assigned U.S. Pat. No. 5,149,552, issued Sep. 22, 1992, which describes certain calcium citrate salt crystals.

BACKGROUND OF THE INVENTION

Vegetable oils are most desirable natural forms of lipids to be used for diet purpose. The role of lipids, i.e. fats, which are saturated or comprise trans unsaturated fatty acid glycerides in blood circulatory problems is well known. The use of vegetable oils which are comprised of cis-unsaturated fatty acid triglyceride in lieu of the aforesaid saturated fats or trans-unsaturated fatty acid triglycerides has been highly recommended to avoid the blood circulatory problems of the latter fats.

One of the difficulties in implementing this recommendation is the physical form of the desirable vegetable oils, i.e., liquid form which is not always adaptable for many food uses. In the past, vegetable oils have been converted to the more useful semi-solid to solid state by hydrogenation which results in conversion of the vegetable oils to saturated fat and trans-unsaturated fatty acid glycerides. Therefore, the use of the desirable vegetable oils has been seriously limited in the food industry to only those situations where the liquid oil can be employed.

The dietary importance of low-fat, low-calorie, no cholesterol foods is well-documented in not only the scientific literature but also in the lay press. Considerable research effort has been, and is now being, expended to meet the requirements of new food technology. Thus, low fat food products such as cheeses, mayonnaise, salad dressings, margarines and the like have been developed based on non-fat substitutions in whole or in part for the fat content of classical foods. Such products necessitate new food additives and constituents of the new dietary food compositions. These new additives and constituents are mainly designed to improve appearance, color, mouth-feel, and induce other properties to assure public acceptability of the new dietary compositions. To be successful, such additives and constituents should be food acceptable and compatible with the compositions in which they are employed. For example, titanium dioxide has been used as a whitener in low fat compositions and is found to be compatible in these compositions. However, the food acceptability of titanium dioxide has been challenged and is rejected in many countries, especially in Europe.

SUMMARY OF THE INVENTION

The present invention provides new and useful vegetable oil calcium citrate salt compositions which are readily adaptable for use in food compositions, particularly as opacifiers, whitening agents and partial fat substitutes. These and other uses of the present new salt compositions are described hereinafter.

The invention provides semi-solid to solid oil-calcium citrate compositions which are readily adaptable for use in the food industry, thus providing the benefits of natural vegetable oil and mineral oil which heretofore was not possible. The products thus produced can be made to range from a somewhat viscous consistency, e.g. mayonnaise consistency, to a solid consistency (similar to lard) by simply adjusting the level of ingredients employed in the compositions.

DETAILED DESCRIPTION OF THE DRAWINGS

Figure 1:
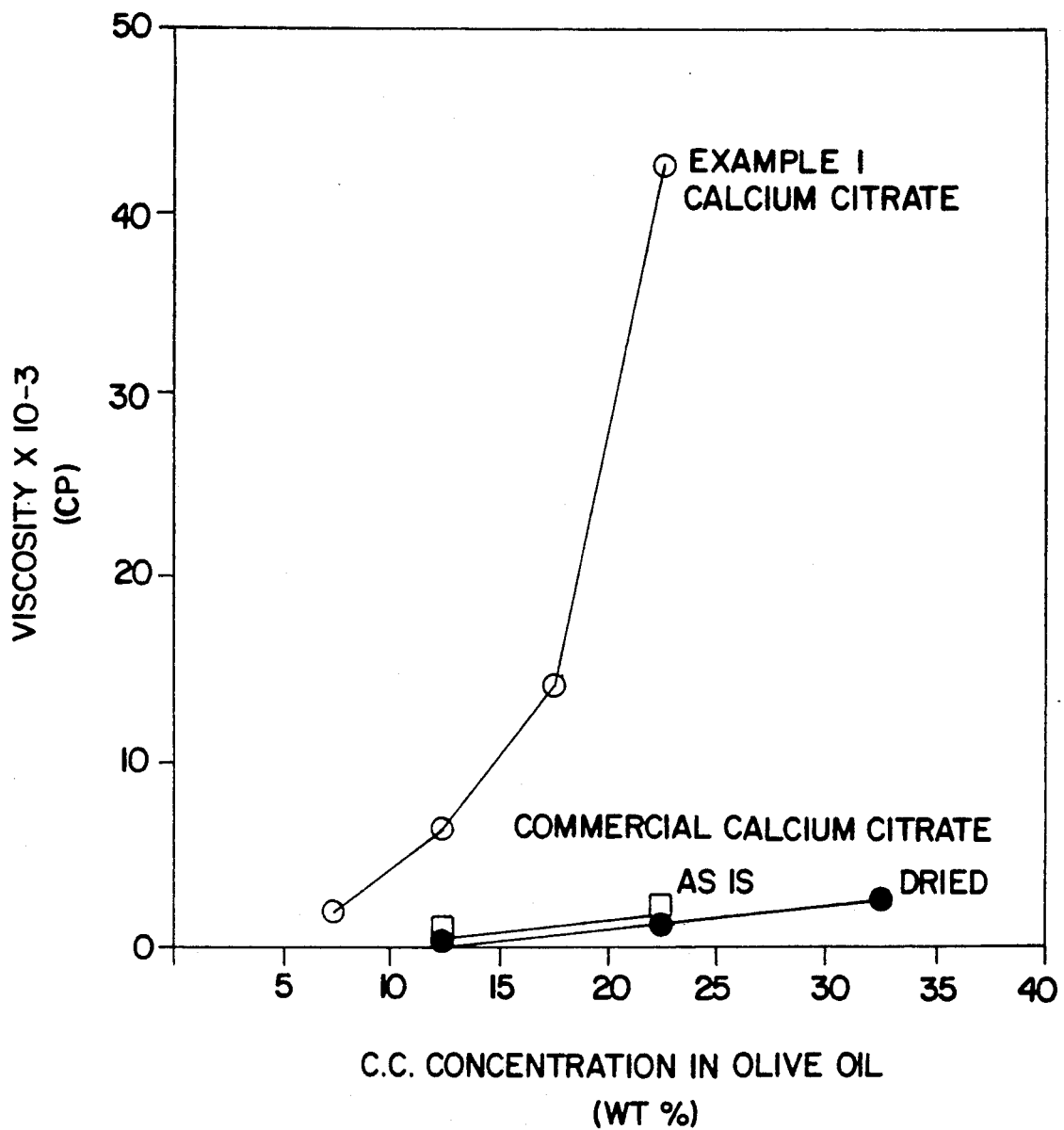

In the accompanying drawings, FIG. 1 is a plot of viscosity of olive oil at varying concentrations of the specific calcium citrate employed in the present new oil compositions of the inventions (the unfilled circle plot) and commercial calcium citrate, hydrated (the square plot) and the dehydrated form (the black circle plot).

Figure 2:
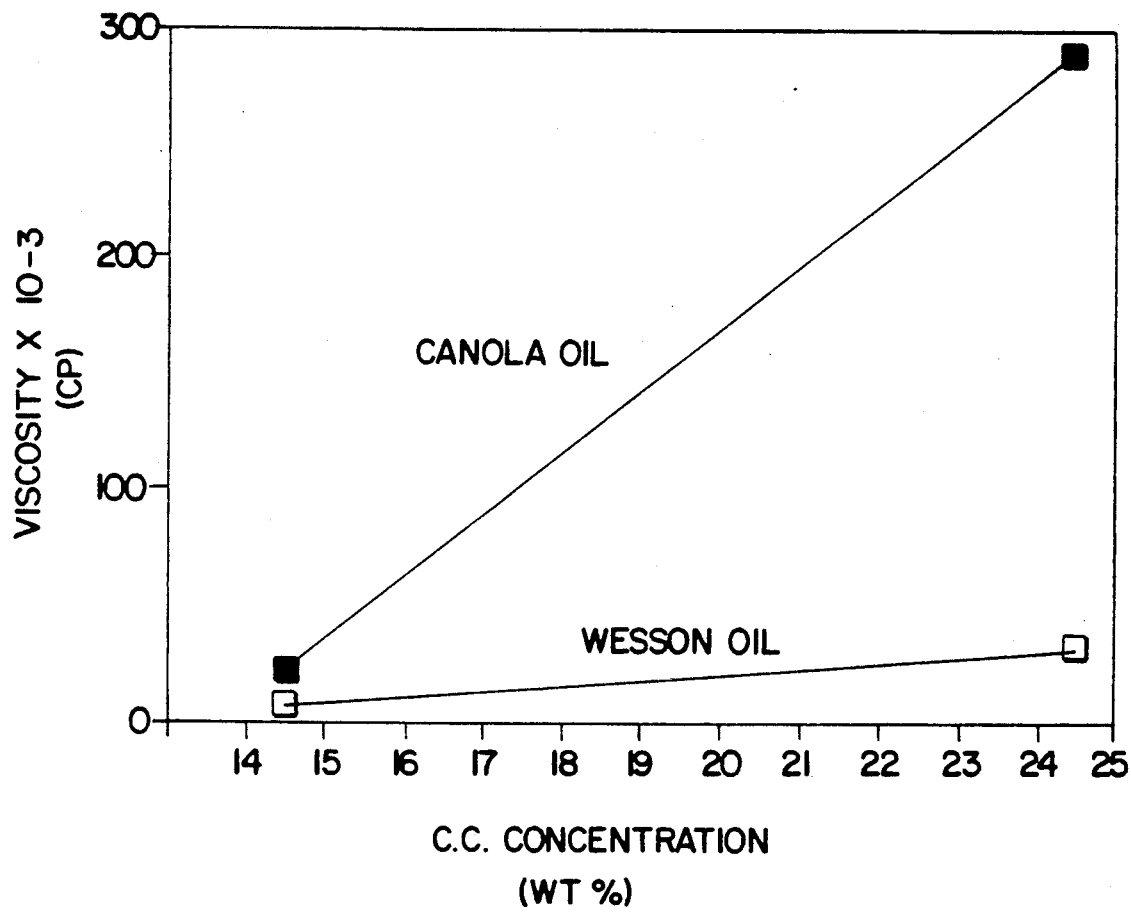

FIG. 2 is a plot of viscosity of the present new compositions against concentration of calcium citrate for soybean oil (the unfilled square plot) and canola oil (the black square plot).

DETAILED DESCRIPTION OF THE INVENTION

The present new vegetable oil based compositions comprise water and a finely divided calcium citrate salt reaction product. A further embodiment of this invention are vegetable oil based compositions comprising water, a finely divided calcium citrate salt reaction product and a carbohydrate-base ingredient.

The finely divided calcium citrate salt used herein is the reaction product of a calcium compound selected from the group consisting of calcium hydroxide, calcium oxide and calcium carbonate with citric acid wherein the reaction product has a mole ratio of calcium to citric acid from 2.5:2 to 2.95:2, preferably 2.61:2 to 2.92:2 and a pH value in a 1% water slurry of said reaction product from about 4 to below 7, preferably about 4 to about 5.5.

In general, these calcium citrate crystals are prepared by spray drying a neutralization mixture prepared by neutralizing citric acid with a slurry of calcium oxide/or hydroxide in water, i.e., a slurry of calcium hydroxide under controlled conditions to assure the production of the present new calcium citrate salts. Calcium carbonate can be used to neutralize citric acid, but slow additions and/or large reaction vessels are required to prevent overflow of the reaction mixture due to liberation of carbon dioxide. Temperature, slurry solid content and agitation time before spray drying are critical parameters in determining the physical characteristics of final product.

In particular, the calcium citrate crystals are prepared by first neutralizing citric acid with calcium hydroxide while controlling the rate and conditions of the reaction as well as the degree of neutralization. In the present process, a calcium hydroxide aqueous slurry is reacted with a citric acid solution in water resulting in a strong exothermic reaction. The rate of reaction, concentration of reactants and reaction conditions are all important factors in producing calcium citrate salts of the desired pH values and particle size.

It is preferred to form two separate aqueous systems, one a solution of citric acid and the second, a slurry of calcium hydroxide, and then mix the uniform slurry of calcium hydroxide with the aqueous citric acid. The temperature of the mixture is not allowed to exceed about 60° C. The pH of the slurry so produced after thorough mixing should fall within the range of 4–6 and, if needed, should be adjusted to this range of pH. The slurry is then used in the spray drying step.

The produced calcium citrate salts are very insoluble in water providing about 0.1% by weight solution at ambient temperature and slightly more soluble in hot water. During preparation of a batch and while waiting for spray drying of the batch, the salts are present in the insoluble form, a slurry of tiny crystals which form aggregates of varying particle size ranging from 5 to 100 microns. In present experience, the best products are obtained by using the following conditions.

The solids level of the aqueous slurry of calcium citrate salt is maintained at 20-26% and preferably at 22-24% by weight based on anhydrous salt. The slurry temperature during spray drying is from 80°-100° F. and preferably 80°-90° F. To avoid gel forming in the aqueous slurry, especially at temperature below 70° F, and recrystallization which can occur on prolonged storage, spray drying of the aqueous slurry is effected within about 4-5 hours after slurry preparation. The slurry is spray dried at an inlet temperature of from about 425° to about 460° F. to deliver a free-flowing white powder with a bulk density of from about 0.3 to about 0.7 g/cc. Extensive mixing and especially homogenization prior to spray drying should be avoided since the particles of salt may be broken down into fine particles and a gel may form.

The calcium citrate crystals generally have the following characteristics:

| | |
|---|---|
| Bulk Density | 0.33-0.66 g/cc |
| Granulation | 95% through U.S. 100 mesh or 150 microns |
| Rotatap, 8 min. | 10% maximum through U.S. 400 mesh or 38 microns |
| pH (1% by weight solution) | 4.0-6.5 |
| Appearance | free-flowing, white powder |

These salts are neutral or slightly acidic and have a well-defined crystal size. The salt can be employed in the form of the anhydrous salt or the hydrated salt. In the hydrated form, the salt can usually contain up to about 13-15% by weight of water of hydration. In general, it is preferred to use the salt in lower hydrated form with less than about 10% by weight of water of hydration. Of course, the hydrated salt can be dried to any level of water of hydration using known methods. In standing, the salt does not undergo any loss or gain of water during storage.

The concentration of salt in the present new compositions can range from about 0.5% to about 35% by weight of the composition. Particularly desirable are compositions wherein the concentration of salt is from about 15% to about 20%. Such compositions have a high ratio of salt to oil and can be used most efficiently in providing desired levels of the salt in the food compositions to which they are added, as described hereinafter.

The calcium citrate employed in the present invention is in the form of small crystalline platelets. The average length of the crystals is below 3.0 microns, preferably about 1.5 microns, width below 2.0 microns, preferably about 1 micron and thickness below 1 micron, preferably 0.1 to 0.2 micron. During preparation, clusters of these tiny platelets aggregate together to form spherical particles that range from about 5 to about 50 microns in diameter. Such clusters are readily separable by mechanical stirring in oil or by merely allowing the clusters to stand in oil for protracted periods of time, e.g. overnight at room temperature. A most efficient method for reducing the clusters to the individual platelets is the use of mechanical shear, as provided, for example, by a ball mill. Other mechanical stirring means that can be employed include homogenizers, microfluidizers, or colloid mills.

When mixed with vegetable oil, particularly at levels above about 10% by weight, the present calcium citrate salt platelets cause a significant increase in the viscosity of the mixture. Thus, at 15% to 20% by weight, the oil-calcium citrate compositions are in the form of thick pastes resembling soft cheeses and margarines in consistency. At 20% and higher levels, the mixtures tend to solidify, to a lard texture, especially when highly efficient mechanical shear is used.

It has been discovered that on the addition of water, i.e., about 0.1% to about 10% by weight, preferably about 0.5% to about 3% by weight, to a vegetable oil based composition containing the calcium citrate reaction product, significant increases in viscosity are achieved over non-water containing vegetable oil based compositions containing the calcium citrate reaction product. It has been further discovered that on the addition of carbohydrate based ingredients, i.e., about 5% to about 60%, preferably about 15% to about 40% by weight to a vegetable oil based composition containing the calcium citrate reaction product about 0.5 to about 20% by weight, preferably about 3% to about 10% by weight in combination with water, i.e., about 0.1% to about 35%, preferably about 0.1% to about 25% by weight. This combination permits more water to be present and yet provide higher viscosity products and low calorie products such as margarine-like pastes useful as antisticking and laminating agents, especially in baking.

An additional modification of the products of this invention is the addition of edible emulsifiers in amounts ranging from about 0.1% to about 2%, preferably 0.2% to about 1% by weight. The edible emulsifiers which can be utilized include known monoglycerides, diglycerides, sodium stearoyl lactylate, calcium stearoyl lactylate, lecithin, sugar esters and the like. The addition of the emulsifiers provide better mix of ingredients and better overall products.

The carbohydrate-based ingredients used herein include flour and refined products including natural occurring and refined flours, cellulose and food gums as well as modified product such as starches, dextrins, maltodextrins, and the like.

In one preferred modification, the calcium citrate platelets are coated with a food acceptable additive capable of coating the platelets. A wide variety of such coating additives can be used for this purpose and include, for example, protein coatings such as casein, sodium caseinate and zein; polysaccharide gums such as xanthan gum, gum arabic, locust bean gum, guar and similar gums; higher fatty acids, e.g. $C_{12}$-$C_{22}$ such as lauric acid, stearic acid, oleic acid, linoleic acid, or sodium or potassium salts of these higher fatty acids; natural food solids such as milk solids and fruit juices such as orange juice solids; and cellulose gums, such as methyl cellulose, ethyl cellulose and carboxymethyl cellulose. Coating of the calcium citrate platelets can be accomplished using art-recognized techniques. The coating agent can be added to an aqueous suspension of the platelets after being produced and the resultant mixture then spray dried. Alternatively, before spray-drying of the calcium citrate suspension in water before and/or during preparation of the new salt, the coating agent can be added to the reaction mixture and the spray-dried product obtained in coated form. A third procedure is to add the coating agent to the dry calcium citrate salt during the milling step in the oil. A further procedure involves addition of the coating agent to the food composition to which the present new food additive vegetable oil compositions are added and the salt platelets are coated in situ during dispersion in the food composition.

The present new compositions are particularly effective as opacifier and whitening agents for oil-based food compositions. Exemplary such food compositions include puddings, mayonnaise, salad dressings and similar products in which saturated fat is mostly replaced by vegetable oil. When used as an opacifier-whitener, the levels of salt should be from about 0.2% to 5.0% of the food composition.

To attain such levels of salt for opacifier-whitener uses, the salt can be added neat to the food composition. Alternatively, and preferably, the salt is added in the form of the new vegetable oil calcium citrate pastes of this invention. The use of the paste assures the highly desirable form of platelets of the calcium citrate which are responsible for the opacifier-whitener results in the aqueous food composition. The paste is preferably comprised of from about 15% to about 30% by weight salt.

In either form of addition, the calcium citrate crystals are distributed uniformly throughout the food composition by usual mixing methods and no special handling is required to accomplish this result.

In addition to use as a whitener and opacifier, the present new oil salt compositions are useful as potential fat substitutes. The oil-calcium citrate compositions are produced with viscosities and flow properties that vary from a soft smooth texture as mayonnaise and butter spreads to fairly hard textures like lard and roll-in margarines. It enables the consumer to replace hydrogenated fats and animal fat by healthy, untreated vegetable oils.

A further use of the present new vegetable oil calcium citrate compositions is as an anti-sticking agent, particularly for baking products such as cookies, breads and cakes. In this use, the oil-based paste is merely applied to the surface of baking trays in contact with the product to be baked and serves as an effective anti-sticking agent. The layer of paste applied can be a very thin layer formed by merely spreading the oil salt composition substantially uniformly across the baking surface. The baked products are easily removed without contact surface disruption.

In contrast with the results obtained with the calcium citrate crystals of this invention commercial calcium citrate, whether in hydrated form (13% H₂O or moisture) or after rigorous drying, does not exhibit the same oil viscosification properties and is ineffective when tested side-by-side with the present new compositions, or as an additive to food composition.

The mechanism by which the present process operates is not fully known or understood. It is believed, however, that the fatty acids naturally present in almost every oil absorb on the surface of the calcium citrate crystals and help in dispersing the fine particles in the oil. Different vegetable oils behave differently when mixed with calcium citrate of the present invention producing different viscosities. It appears to rely almost completely on the shape, number and geometrical arrangement of the calcium citrate platelets as they disperse in the continuous oil phase. The degree of hardening of the oil can be controlled by the amount of calcium citrate added to the oil and the degree of dispersibility of the fine crystalline platelets. For example, at a weight level of about 20% a mayonnaise texture is obtained using olive oil. At about 26-33% calcium citrate a fairly hard lard-like product is obtained. The new products of this invention are stable whether stored at ambient temperature or in the refrigerator. Flavors and colors can be added to achieve product attributes.

The vegetable oils are well-known and are characterized by ethylenic unsaturation in the fatty acid moieties. Such oils remain liquid over a wide temperature range. Exemplary oils include olive oil, safflower oil, corn oil, canola oil, peanut oil, cottonseed oil, sesame seed oil, soybean oil and poppy seed oil.

The process of the invention is accomplished by subjecting a mixture of the selected vegetable oil with calcium citrate to mechanical shear to increase the viscosity of the mixture by separating the calcium citrate platelets from the clusters. For this purpose micromilling can be employed using classical apparatus designed to provide high shear mixing. Ball mills are generally used for micromilling, e.g. Dyno-Mill machine, which is readily available and is a very efficient dispersing instrument. The number of passes of the mixture of vegetable oil and calcium citrate through the ball mill does not seem to be critical but usually one or two passes will suffice. As the mixture passes through the ball mill it becomes less gritty (grittiness is due to the large clusters of the salt), the viscosity increases significantly, and the temperature of the mixture increases.

The products, as obtained by the instant process, range from semi-solids, e.g. viscous liquids and pastes, to solids, e.g. lard-like. These products are very stable on storage whether at room temperature or at reduced temperatures. The viscosities of these products remain practically unchanged with time, and no change in product smoothness is observed. There is no significant agglomeration of the crystalline platelets.

Rheological investigation of these products revealed interesting properties. The shear stress viscosity curves indicate that these dispersions are shear thinning, while the viscosity temperature curves show no change up to 60° C. with minimal loss of viscosity, thereafter, up to 100° C. There is no melting point for these compositions as exhibited with fats and hydrogenated oils.

Products produced by intimate mixing under high shear of a mixture of vegetable oil with commercially available tricalcium citrate showed little viscosification and shortly after preparation showed significant bleeding which is indicative of instability. Commercial tricalcium citrate contains high levels of water of hydration, e.g. 13% moisture content. Even when the moisture content of such products was removed by vacuum oven-drying the dried salt did not cause viscosification even at high levels in the vegetable oil.

As shown in FIG. 1 of the attached drawings, increasing the concentration of the calcium citrate employed in the present invention causes significant increase in the viscosity whereas the use of hydrated or dry commercial tricalcium citrate resulted in little, if any change in the viscosity of the treated oils, even at 35% by weight of the oil.

The following examples further illustrate the invention.

EXAMPLE 1

A calcium citrate sample was prepared by reacting 2763.8 lbs. of citric acid with 1600 lbs. calcium hydroxide (97-98% Ca(OH)$_2$ by analysis) in the presence of 1433 gallons of water. The mole ratio of calcium hydroxide to citric acid was very slightly less than 3:2, actually 2.92:2. The citric acid (Pfizer fine granular, food grade) was mixed in a large batch tank with 675 gallons of cold water. The calcium hydroxide (Mississippi lime, hydrated lime, food code) was mixed in a separate batch tank with 75 gallons of cold water. The calcium hydroxide slurry is then pumped into the citric acid solution at a rate to deliver the entire slurry in 10-15 minutes. It is necessary to have good agitation during the entire reaction and mixing process. The remaining 83 gallons of water is used to rinse the calcium hydroxide tank and transport lines. Due to the heat of reaction, the temperature of the resultant slurry was increased from an initial value of 15° C. (60° F.) to a maximum of 57° C. (134° F.). After the reaction is complete, the batch is cooled to 80°-90° F. The final pH of this concentrated slurry (22% calcium citrate, dry basis) should fall within the range 3.8-4.6 or can be adjusted up or down using the reacting ingredients. The slurry is then dried via spray drying utilizing a rotary wheel (7600 rpm). The outlet temperature was adjusted to 225° F. and the inlet temperature was 450° F.

The calcium citrate powder obtained after spray drying was a free-flowing white powder with a moisture less than 6.0% and a bulk density in the range 0.33-0.65 g/cc. The pH of 1% slurry in water was 5.5. 95% of the powder passed through U.S. 100 mesh.

EXAMPLE 2

100 g of calcium citrate, prepared according to Example 1, was stirred into 900 g of olive oil (obtained from Filipo Berio & Co., Lucca-Italy) in a 2 liter glass beaker using a Lightnin Labmaster stirrer (model DS3004 by General Signal) at 100 rpm.

A Dyno-mill Type KDL (made by Willy A. Bachofen AG Maschinenfabrik Basel-Switzerland), provided with a cooling jacket, was preconditioned by running olive oil through the mill for a few minutes before starting the grinding. The calcium citrate/olive oil suspension was then fed slowly through the mill at the rate of about 150 g/min. During milling the temperature of the suspension was increased while the grittiness of the calcium citrate was greatly reduced. Viscosity measurement was made for this 10% calcium citrate in olive oil using Brookfield viscometer (Brookfield Digital Viscometer Model DV-II Stoughton, MA 02072) and found to be 1,920 centipoise (cp.) at room temperature (ca. 20° C.) and a T-F spindle at 5 rpm. It is evident that the fine dispersion of calcium citrate has increased the viscosity of olive oil by a factor of about 23, even at a 10% level in the oil. the viscosity of olive oil at 20° C. is 84 cp. (CRC Handbook of Chemistry and Physics).

EXAMPLE 3

Example 2 was repeated at various calcium citrate and olive oil ratios ranging from 10% to 25%. Exactly the same grinding procedure was followed, and the viscosities at room temperature (70° F.) of the resulting pastes are given below.

| Concentration of Calcium Citrate (%) | Brookfield Viscosity (cps) | Oil Viscosification Factor |
|---|---|---|
| 10 | 1.9 × 10$^3$ | 23 |
| 15 | 6.4 × 10$^3$ | 76 |
| 20 | 14.2 × 10$^3$ | 169 |
| 25 | 42.6 × 10$^3$ | 507 |

The table clearly shows that olive oil viscosity is drastically increased by up to 500 times its normal value when micromilled calcium citrate of this invention is dispersed in the oil. The texture of these oil-calcium citrate compositions was smooth enough to spread on bread slices to give the appearance and eating quality of mayonnaise and/or butter. The viscosity of the 25:75 calcium citrate-olive oil remained practically constant over the temperature range of 25° C. to 50° C. On the other hand, the viscosity of untreated olive oil decreased by a factor of more than 2.

EXAMPLE 4

The 15% calcium citrate in olive oil paste made in Example 3 was passed again through the Dyno-mill for up to 4 grinding cycle to study the effect of these passes on viscosity. Hardening (or viscosification) of the oil was found to be not significantly dependent on the number of passes at that concentration of calcium citrate.

EXAMPLE 5

A commercial calcium citrate tetrahydrate purchased from Merck Co. (13.3% moisture content) was ground at concentrations of 15% and 25% in olive oil. Exactly the same grinding procedure was followed as in Example 2. A highly homogeneous liquid product was obtained with respective viscosities of 0.88×10$^3$ and 2.16×10$^3$ cps. Thus, no appreciable viscosification was found. These viscosity values are much lower than the corresponding values given in Example 3 by a factor of up to 20. After about three days significant bleeding occurred in these samples. Bleeding is an indication of dispersion instability and the salt particles separated from the continuous oil phase, which did not occur in the Example 3 compositions.

EXAMPLE 6

1 Kg of the commercial calcium citrate used in Example 5 was vacuum oven-dried at 23 mm Hg and at 220° F. for 48 hours to remove hydrated water. Example 2 was then repeated at 15%, 25% and 35% concentrations of the dry commercial calcium citrate in olive oil. Samples were milled exactly as described in Example 2. In this example each sample was passed through the mill twice. Unlike Example 3, there was no appreciable viscosification found even at 35%. Significant bleeding occurred in these samples after three days. Viscosities of the products obtained, however, are plotted in FIG. 1. The commercially available calcium citrate did not increase the viscosity of olive oil enough to behave like margarine or butter even at the 35% level. At the 35% level, the commercial calcium citrate is about 16 times less viscous than that achieved by only 25% level of calcium citrate according to this invention.

EXAMPLE 7

Example 2 was repeated at 15% and 25% of calcium citrate each in Wesson oil (soybean oil) and canola oils. Pasty, highly viscous materials were obtained. The viscosities, as obtained using Brookfield viscometer, are plotted in FIG. 2. Viscosity was found to increase with concentration. The canola oil showed the highest viscosification factors by inclusion of micromilled calcium citrate of this invention. At 25% calcium citrate/75% canola oil a fairly hard, lard-type solid was obtained of a viscosity that is more than 1000 times more viscous than the starting canola oil at room temperature.

EXAMPLE 8

Various samples of vegetable oil and calcium citrate with different additive coatings were prepared as in the preceding examples and viscosity determined as in Example 2 with the following results:

| Samples Milled[1] | Viscosity (1 day old) (in centipoises) |
|---|---|
| C.C./soybean oil[2] 19.6%   80.4% | Lard-type texture |
| C.C./gum arabic/olive oil 15%   2%   83% | $11.8 \times 10^3$ |
| Spray-dried C.C. (Example 1) gum arabic/orange juice/olive oil[3] | $9.5 \times 10^3$ |
| C.C./ethyl cellulose/olive oil 15%   4%   81% | $3.6 \times 10^3$ |
| C.C./gum arabic/olive oil 15%   5%   80% | $14.6 \times 10^3$ |
| C.C./carboxymethyl cellulose/olive oil 25%   5%   70% | $23.4 \times 10^3$ |
| C.C./canola oil/soybean oil 15%   17%   68% | $5 \times 10^3$ |
| C.C./olive oil/oleic acid 15%   84%   1% | $4.3 \times 10^3$ |
| C.C./olive oil/stearic acid 15%   84%   1% | $3.9 \times 10^3$ |
| C.C./olive oil/sodium caseinate 25%   70%   5% | $69.4 \times 10^3$ |
| C.C./olive oil/stearic acid 25%   74%   1% | $20 \times 10^3$ |
| C.C./olive oil/oleic acid 25%   74%   1% | $26.5 \times 10^3$ |
| C.C./olive oil/zein 25%   70%   5% | $19.4 \times 10^3$ |
| C.C./olive oil/Fibersol II[4] 19%   58%   23% | $320 \times 10^3$ |
| C.C./olive oil/Micropore Buds 515[5] 19%   58%   23% | $36 \times 10^3$ |

[1] The abbreviation, C.C., denotes calcium citrate prepared in accordance with Example 1.
[2] The calcium citrate was coated with sodium stearate at a level of 2%.
[3] The spray-dried calcium citrate (18.9 parts) was coated with gum arabic (2 parts) and orange juice (2 parts), and the coated calcium citrate was used at a level of 15% with the oil at 85%. This sample was not milled.
[4] Fibersol II: A modified dextrin (Matsutani Chemical Industries, Hyogo-ken, Japan)
[5] Micropore Buds 515: A maltodextrin produced by A.E. Staley Manufacturing Company, Decatur, IL).

EXAMPLE 9

TCC HARDENED OIL REPLACEMENT FOR ROLL-IN MARGARINE IN BAKED GOODS 348 g of micromilled calcium citrate in olive oil (32% salt) was spread over a Sweet Danish dough (1500 g) and rolled in. Sample was then retorted for 30 minutes, flattened, and rolled. This procedure was repeated three times in order to form multiple layers. The viscosity of the calcium citrate/olive oil sample was high enough (close to roll-in margarine) that there was no squeezing of oil out of the dough.

The dough was then made into Swiss Rolls, proofed for 45 minutes, and then baked for 20 minutes. After baking and allowing to cool to room temperature, the Swiss rolls that resulted were stored in boxes at room temperature. Samples were compared to control made with margarine the second day. There was no discernible difference found between the margarine control and that made with calcium citrate/oil in appearance, layer formation, and taste.

This example shows that calcium citrate hardened non hydrogenated oils can be used to replace margarine, a hydrogenated oil that is highly saturated with trans fatty acids. In addition, these samples provide about 30% less fat since equal weight of margarine and the salt/oil dispersions were used to produce the Sweet Danish.

EXAMPLE 10

EFFECT OF ADDED WATER ON THE VISCOSITY OF CALCIUM CITRATE DISPERSED IN VEGETABLE OIL 200 grams of calcium citrate, prepared according to Example 1, was stirred into 800 grams of canola oil in a liter glass beaker using a Lightnin Labmaster stirrer at 100 rpm.

A Dyno-mill Type KDL (made by Willy A. Bachofen AG Maschinenfabrik Basel-Switzerland), provided with a cooling jacket, was preconditioned by running canola oil through the mill for a few minutes before starting the grinding. The calcium citrate/canola oil suspension was then fed slowly through the mill at the rate of about 150 grams/minute. During milling the temperature of the suspension was increased while the grittiness of the calcium citrate was greatly reduced.

100 gram aliquots of the above viscosified oil were weighed with water included in them at increasing levels. After the water addition, each sample was mixed for 4 minutes until uniform. Viscosity measurements were made for these calcium citrate-canola oil-water systems using Brookfield viscometer at room temperature (ca. 20° C.) and a T-D spindle at 5 rpm.

The viscosity data as function of added water, up to 5%, is listed below. A very significant increase in viscosity of the micromilled calcium citrate-canola oil mixture is evident even at the addition of a fraction of a percentage of water. A maximum in viscosity (24 fold increase) is obtained in this blend of calcium citrate-canola oil at about 1% added water. Additions of higher levels of water, up to 5%, showed an increase in viscosity over the control but not as high as the 1% water addition. For these food systems containing only calcium citrate and vegetable oil, the added water appears to be associated with calcium citrate and thus dispersibility of the microcrystals of calcium citrate. Some phase separation was evident at the 5% water addition.

This point will be more evident in the following examples where systems were developed to tolerate more water additions. It should be noted that the water levels mentioned in Example 10 are added over and above the moisture content of the spray-dried calcium citrate used in this Example as prepared in Example 1 of this invention.

| Extra Water Added (%) | Viscosity ×10$^{-3}$ (CPS) |
| --- | --- |
| 0 | 17.0 |
| 0.1 | 67.3 |
| 0.3 | 116.3 |
| 0.5 | 196.0 |
| 1.0 | 412.0 |
| 1.25 | 160.0 |
| 1.5 | 167.0 |
| 2.0 | 148.0 |
| 3.0 | 103.3 |
| 3.5 | 103.3 |
| 5.0 | 31.7 |

EXAMPLE 11

EFFECT OF WATER ON THE VISCOSITY OF MICROMILLED CALCIUM CITRATE IN VEGETABLE OIL/FLOUR MIXTURES 200 grams of calcium citrate of Example 1 were mixed with 800 grams canola oil (obtained from PET Inc., St. Louis, Mo.) and micromilled in a Dyno-mill. One pass was sufficient to provide a fairly viscous dispersion.

200 grams of the above micromilled calcium citrate-canola oil was weighed and added to 480 grams of wheat flour (patent type) and mixed together with a wide spatula. An additional 320 grams of canola oil were weighed and added to this blend while mixing to produce a 1000 gram composition made of; calcium citrate =5%, canola oil=47%, patent flour=48%.

Given samples were then taken from the above mixture and titrated with varying amounts of water to produce 100 gram samples. The viscosities of these different samples were measured using Brookfield viscometer.

| EXTRA WATER ADDED (%) | VISCOSITY ×10$^{-3}$ (CPS) |
| --- | --- |
| 0 | 4.9 |
| 1.0 | 11.6 |
| 1.5 | 16.7 |
| 2.0 | 22.5 |
| 2.5 | 31.5 |
| 3.0 | 66.7 |
| 5.0 | 426.5 |
| 10.0 | 636.7 |
| 20.0 | 571.0 |
| 40.0 | 113.9 |

The data shows a significant increase in viscosity with addition of small levels of water to this calcium citrate canola oil-flour system. A 130 fold increase in viscosity was achieved by the inclusion of an extra 10% water in the mixture (636, 700 cps for the 10% vs. 4,900 cpm for 0% water addition). A very stable viscous and homogeneous system was obtained at the 10% water addition. At the 20% water addition, the viscosity was slightly below the 10% water addition but still much higher than the control. Signs of phase separation started at this point that became much evident at the 40% water addition. At that high water level, a whitish color starts to appear due to a phase inversion as evident by the significant drop of viscosity to 113, 900 cps from a peak of 636,700 cps.

EXAMPLE 12

ROLE OF CALCIUM CITRATE IN VISCOSITY BUILD-UP WITH WATER ADDITIONS

To demonstrate the role of calcium citrate of Example 1 in providing not only higher viscosities but increased stability and smoothness of hardened vegetable oils, the following experiments were run. Three samples with a 5% micromilled calcium citrate and three samples without calcium citrate were prepared following Example 11. However, the canola oil level was fixed at 43–44% by weight in all six samples. Also, a pastry flour was used in this Example and three levels of added water were used, 0, 5 and 10%, in the two sets of experiments.

The compositions and viscosities of the six samples are given below.

| | COMPOSITION | | | | |
| --- | --- | --- | --- | --- | --- |
| SAMPLE | CALCIUM CITRATE (%) | CANOLA OIL (%) | PASTRY FLOUR (%) | ADDED WATER (%) | VISCOSITY ×10$^{-3}$ (CPS) |
| A | 5 | 44.2 | 50.8 | 0 | 19.2 |
| B | 5 | 44.2 | 45.8 | 5 | 317.0 |
| C | 5 | 44.2 | 40.8 | 10 | 342.0 |
| D | 0 | 43.0 | 57.0 | 0 | 8.8 |
| E | 0 | 43.0 | 52.0 | 5 | 57.3 |
| F | 0 | 43.0 | 47.0 | 10 | 91.0 |

The viscosity data clearly show the significant role of water in increasing the viscosity of the calcium citrate containing oil samples. The 5% addition of water produced more than 16 fold increase in viscosity of the citrate containing samples versus a 6.5 fold increase for the controls with no calcium citrate. In addition, both the spreadability and smoothness were made more significant for the calcium citrate containing samples than the controls. The superior lamination properties of the calcium citrate-hardened oil samples of this Example are evident when used in a croissant pastry as shown in Example 13.

EXAMPLE 13

A dough comprising of

| | | |
|---|---|---|
| Remarkable flour | 1000 g | |
| Salt | 20 g | |
| Yeast | 12 g | |
| Sugar | 25 g | |
| Water | 630 g | | was formed and allowed to ferment for 1 hour. 250 gram samples of this dough were scale weighed. Each dough sample was smoothened to about 5×12 inch flats and ⅔ of it was covered with 60 grams of hardened canola oil of Example 12. The flattened dough sheet was then folded twice, sheeted out and placed in refrigerator to relax for about 30 minutes. This procedure was repeated until about 54 layers were formed. Sample was then cut and shaped into croissant pastry and baked at 135° F. for 18 minutes.

Evaluation of the baked croissant samples showed significantly improved lamination in the calcium citrate containing oils as compared with the controls without calcium citrate. Puffing (larger baked volume) was higher with increasing level of water in the viscosified canola oil.

EXAMPLE 14

203.6 grams of calcium citrate of Example 1 were mixed with 794.4 grams of canola oil and micromilled in Dyno-mill as in Example 2.

19.6 grams of the above micromilled calcium citrate-canola oil were weighed and added to 40.75 grams of Waxy starch No. 1 (obtained from A. E. Staley Manufacturing Co., Decatur, Chicago) and mixed together with a wide spatula. An additional 29.65 grams of canola oil were weighed and added to this blend while mixing. At that step, 10 grams of water was added and mixed to produce 100 grams (sample A).

Similarly, 100 grams of other compositions; sample B (with pastry flour) and sample C (with Tapioca starch obtained from Staley Manufacturing Co.) were made by the same procedure. The compositions and viscosities of samples A, B and C are given below.

| SAMPLE | COMPOSITION (%) | | VISCOSITY ×10⁻³ (cps) |
|---|---|---|---|
| A | Calcium citrate | 4 | 100 |
| | Canola oil | 45.25 | |
| | Waxy starch | 40.75 | |
| | Water | 10 | |
| B | Calcium citrate | 4 | 317 |
| | Canola oil | 45.25 | |
| | Pastry flour | 40.75 | |
| | Water | 10 | |
| C | Calcium citrate | 4 | 140 |
| | Canola oil | 45.25 | |
| | Tapioca starch | 40.75 | |
| | Water | 10 | |

The above data suggest that pastry flour, at the same level, produce higher viscosity than Waxy and Tapioca starches.

Waxy starch produces a very unusually smooth paste in combination with oil and calcium citrate. The textural quality of paste is very high and makes spreadability to be superior on application to dough lamination. In addition, we found that calcium citrate need no milling in oil when used in combination with this waxy starch. The particle size of the calcium citrate cluster is reduced; as evident by lack of grittiness.

The samples above were stable to laminate Danish Rolls.

EXAMPLE 15

250 grams of calcium citrate made in example 1 was dispersed in 750 grams of canola oil and micromilled as in Example 2.

To 200 grams of this 25% calcium citrate-oil dispersion, 3 grams of xanthan gum and 3 grams of sodium stearoyl lactylate (emulsifier) were added and mixed properly. While still mixing, 15 grams of water was slowly added. Mixing was continued until the system became homogeneous to produce a stable composition of:

| | |
|---|---|
| Calcium citrate | 22.6% |
| Canola oil | 67.9 |
| Water | 6.8 |
| Xanthan gum | 1.35 |
| Emplex (sodium stearoyl lactylate) | 1.35 |

What is claimed is:

1. A vegetable oil-based composition comprising from about 0.1% to about 10% by weight of water and 0.5% to about 35% by weight of a finely divided calcium citrate salt, said salt being a reaction product of a calcium compound selected from the group consisting of calcium hydroxide, calcium oxide and calcium carbonate with citric acid wherein said reaction product has a mole ratio of calcium to citric acid from 2.5:2 to 2.95:2 and a pH value in a 1% water slurry of said reaction product from about 4 to below 7 at 25° C.

2. A composition according to claim 1 wherein water is present from about 0.5% to about 3% by weight.

3. A composition according to claim 2 wherein the edible emulsifier is present from about 0.5% to about 1% by weight.

4. A composition according to claim 1 wherein an edible emulsifier is present from about 0.1% to about 2% by weight.

5. A composition according to claim 1 wherein the amount of said salt is from about 20% to about 20% by weight of the composition.

6. A vegetable oil-based composition comprising from about 0.1% to about 35% by weight of water, about 0.5% to about 20% by weight of a finely divided calcium citrate salt, said salt being a reaction product of a calcium compound selected from the group consisting of calcium hydroxide, calcium oxide and calcium carbonate with citric acid wherein said reaction produce has a mole ratio of calcium to citric acid from 2.5:2 to 2.95:2 and a pH value in a 1% water slurry of said reaction product from about 4 to below 7 at 25° C. and a carbohydrate-based ingredient from about 5% to about 60% by weight.

7. A composition according to claim 6 wherein said reaction product has a mole ratio of calcium to citric acid from about 2.61:2 to about 2.92:2.

8. A composition according to claim 6 wherein a 1% water slurry of said salt shows a pH value of from about 4.0 to about 5.5.

9. A composition according to claim 6 wherein the amount of said salt is from about 3% to about 10% by weight of the composition.

10. A composition according to claim 6 wherein said water is present from about 0.1% to about 25% by weight, said calcium citrate salt reaction product is present from about 3% to about 12% by weight of water and said carbohydrate-based ingredient is present from about 15% to about 40% by weight.

11. A composition according to claim 10 wherein said carbohydrate-based ingredient is starch.

12. A composition according to claim 10 wherein said carbohydrate-based ingredient is selected from the group consisting of naturally occurring flour and refined flour.

13. A composition according to claim 10 wherein an edible emulsifier is present from about 0.2% to about 1% by weight.

14. A composition according to claim 6 wherein said carbohydrate-based ingredient is starch.

15. A composition according to claim 6 wherein said carbohydrate-based ingredient is selected from the group consisting of naturally occurring flour and refined flour.

16. A composition according to claim 6 wherein an edible emulsifier is present from about 0.1% to about 2% by weight.

* * * * *